US012788633B2

(12) United States Patent
Van Der Mooren et al.

(10) Patent No.: US 12,788,633 B2
(45) **Date of Patent: *Nov. 10, 2026**

(54) BLEB CONTROL GLAUCOMA SHUNTS

(71) Applicant: AMO GRONINGEN B.V., Groningen (NL)

(72) Inventors: Marrie Van Der Mooren, Engelbert (NL); Theophilus Bogaert, Groningen (NL)

(73) Assignee: AMO GRONINGEN B.V., Groningen (NL)

( * ) Notice: Subject to any disclaimer, the term of this patent is extended or adjusted under 35 U.S.C. 154(b) by 478 days.

This patent is subject to a terminal disclaimer.

(21) Appl. No.: 18/332,703

(22) Filed: Jun. 9, 2023

(65) Prior Publication Data

US 2023/0310212 A1 Oct. 5, 2023

Related U.S. Application Data

(62) Division of application No. 16/171,285, filed on Oct. 25, 2018, now Pat. No. 11,672,701.

(51) Int. Cl.
*A61F 9/007* (2006.01)
*A61L 31/16* (2006.01)

(52) U.S. Cl.
CPC .......... *A61F 9/00781* (2013.01); *A61F 9/007* (2013.01); *A61F 2240/001* (2013.01); *A61F 2250/0067* (2013.01); *A61L 31/16* (2013.01)

(58) Field of Classification Search
CPC .................. A61F 9/00781; A61F 9/007; A61F 2240/001; A61F 2240/0067; A61L 31/16; A61L 2300/40
See application file for complete search history.

(56) References Cited

U.S. PATENT DOCUMENTS 3,915,172 A 10/1975 Wichterle et al.
4,030,480 A 6/1977 Meyer
(Continued)

FOREIGN PATENT DOCUMENTS

AU 2016228241 A1 10/2016
FR 2233028 A1 1/1975
(Continued)

OTHER PUBLICATIONS

Alder, "Intraocular Pressure," Alder's Physiology of the Eye, 1995, vol. 5, pp. 249-277.
(Continued)

*Primary Examiner* — Philip R Wiest

(57) ABSTRACT

An implantable glaucoma shunt for treating glaucoma in an eye is disclosed herein. The glaucoma shunt may comprise a plurality of strips adapted to be positioned on a sclera of the eye and an elastomeric drainage tube having an outflow end connected to the plurality of strips and an opening thereof. The drainage tube may have an open lumen and a length sufficient to extend into the anterior chamber of the eye. The plurality of strips may be substantially parallel with one another or the plurality of strips may diverge from one another. In an embodiment, the disclosed glaucoma shunt may be manufactured by removing material from a prior-art type glaucoma shunt. The disclosed glaucoma shunt may be inserted via an insertion tool.

15 Claims, 7 Drawing Sheets

(56) References Cited

U.S. PATENT DOCUMENTS

| | | | | |
|---|---|---|---|---|
| 4,240,434 | A | 12/1980 | Newkirk | |
| 4,298,994 | A | 11/1981 | Clayman | |
| 4,373,218 | A | 2/1983 | Schachar | |
| 4,402,681 | A | 9/1983 | Haas et al. | |
| 4,428,746 | A | 1/1984 | Mendez | |
| 4,457,757 | A | 7/1984 | Molteno | |
| 4,521,210 | A | 6/1985 | Wong | |
| 4,604,087 | A | 8/1986 | Joseph | |
| 4,634,418 | A | 1/1987 | Binder | |
| 4,722,724 | A | 2/1988 | Schocket | |
| 4,729,761 | A | 3/1988 | White | |
| 4,750,901 | A | 6/1988 | Molteno | |
| 4,767,400 | A | 8/1988 | Miller et al. | |
| 4,836,457 | A | 6/1989 | Greiner | |
| 4,863,457 | A | 9/1989 | Lee | |
| 4,865,601 | A | 9/1989 | Caldwell et al. | |
| 4,886,488 | A | 12/1989 | White | |
| 4,902,292 | A | 2/1990 | Joseph | |
| 4,915,684 | A | 4/1990 | MacKeen et al. | |
| 4,932,968 | A | 6/1990 | Caldwell et al. | |
| 4,936,825 | A | 6/1990 | Ungerleider | |
| 4,946,436 | A | 8/1990 | Smith | |
| 4,955,909 | A | 9/1990 | Ersek et al. | |
| 4,968,296 | A | 11/1990 | Ritch et al. | |
| 5,092,837 | A | 3/1992 | Ritch et al. | |
| 5,171,213 | A | 12/1992 | Price, Jr. | |
| 5,178,604 | A | 1/1993 | Baerveldt et al. | |
| 5,192,315 | A | 3/1993 | Jacob-Labarre | |
| 5,282,851 | A | 2/1994 | Jacob-Labarre | |
| 5,300,020 | A | 4/1994 | L'Esperance, Jr. | |
| 5,338,291 | A | 8/1994 | Speckman et al. | |
| 5,372,577 | A | 12/1994 | Ungerleider | |
| 5,397,300 | A * | 3/1995 | Baerveldt | A61F 9/00781 604/8 |
| 5,476,445 | A | 12/1995 | Baerveldt et al. | |
| 5,549,670 | A | 8/1996 | Young et al. | |
| 5,558,629 | A | 9/1996 | Baerveldt et al. | |
| 5,601,094 | A * | 2/1997 | Reiss | A61F 9/00781 604/8 |
| 5,704,907 | A * | 1/1998 | Nordquist | A61F 9/00781 604/8 |
| 5,725,493 | A | 3/1998 | Avery et al. | |
| 5,882,327 | A | 3/1999 | Jacob | |
| 6,050,970 | A | 4/2000 | Baerveldt | |
| 6,203,513 | B1 | 3/2001 | Yaron et al. | |
| 6,261,256 | B1 * | 7/2001 | Ahmed | A61F 9/00781 604/9 |
| 6,471,666 | B1 * | 10/2002 | Odrich | A61F 9/00781 606/108 |
| 6,981,958 | B1 * | 1/2006 | Gharib | A61F 9/00781 604/8 |
| 6,984,392 | B2 | 1/2006 | Bechert et al. | |
| 7,160,264 | B2 | 1/2007 | Lisk, Jr. et al. | |
| 7,207,965 | B2 | 4/2007 | Simon | |
| 7,220,238 | B2 | 5/2007 | Lynch et al. | |
| 7,297,130 | B2 | 11/2007 | Bergheim | |
| 7,357,778 | B2 | 4/2008 | Bhalla | |
| 7,431,710 | B2 * | 10/2008 | Tu | A61F 9/00781 604/9 |
| 7,476,698 | B2 | 1/2009 | Wagener et al. | |
| 7,547,302 | B2 | 6/2009 | Porto et al. | |
| 7,635,358 | B2 | 12/2009 | Tan | |
| 7,641,629 | B2 | 1/2010 | Yuen et al. | |
| 8,353,856 | B2 * | 1/2013 | Baerveldt | A61F 9/00781 604/9 |
| 8,632,489 | B1 * | 1/2014 | Ahmed | A61M 5/14276 604/9 |
| 8,702,639 | B2 | 4/2014 | Van Der Mooren et al. | |
| 8,920,357 | B2 | 12/2014 | Baerveldt et al. | |
| 9,468,558 | B2 | 10/2016 | Baerveldt et al. | |
| 9,999,543 | B2 * | 6/2018 | Wilcox | A61F 9/00781 |
| 10,080,682 | B2 * | 9/2018 | Horvath | A61L 27/54 |
| 11,672,701 | B2 * | 6/2023 | Van Der Mooren | A61F 9/007 604/8 |
| 2005/0107734 | A1 | 5/2005 | Coroneo | |
| 2005/0125003 | A1 | 6/2005 | Pinchuk et al. | |
| 2005/0267398 | A1 | 12/2005 | Protopsaltis et al. | |
| 2007/0293872 | A1 | 12/2007 | Peyman | |
| 2008/0077071 | A1 | 3/2008 | Yaron et al. | |
| 2008/0077238 | A1 | 3/2008 | Deacon et al. | |
| 2008/0200860 | A1 | 8/2008 | Tu et al. | |
| 2014/0066833 | A1 * | 3/2014 | Yaron | A61F 9/00781 604/9 |
| 2015/0100010 | A1 | 4/2015 | Baerveldt | |
| 2015/0313758 | A1 * | 11/2015 | Wilcox | A61F 9/0017 604/8 |
| 2017/0020731 | A1 * | 1/2017 | Baerveldt | A61M 27/002 |
| 2019/0038463 | A1 * | 2/2019 | Kasic | A61F 9/0017 |
| 2020/0129332 | A1 | 4/2020 | Mooren et al. | |

FOREIGN PATENT DOCUMENTS

| | | | |
|---|---|---|---|
| GB | 2101891 | A | 1/1983 |
| GB | 2160778 | A | 1/1986 |
| GB | 2187963 | A | 9/1987 |
| SU | 906561 | A1 | 2/1982 |
| WO | 9112037 | A1 | 8/1991 |
| WO | 9112046 | A1 | 8/1991 |
| WO | 9118568 | A1 | 12/1991 |
| WO | 9320783 | A1 | 10/1993 |
| WO | 9402081 | A1 | 2/1994 |
| WO | 06012009 | A2 | 2/2006 |
| WO | 2007087061 | A2 | 8/2007 |
| WO | 2014033525 | A1 | 3/2014 |
| WO | 2016168686 | A1 | 10/2016 |
| WO | 2017132647 | A1 | 8/2017 |

OTHER PUBLICATIONS

Bickford M.E., "Molteno Implant System, for Patient with Previously Unsuccessful Glaucoms Surgery," Journal of Ophthalmic Nursing Technology, 1987, vol. 6 (6), pp. 224-229.

Davidovski F., et al., "Long-Term Results with the White Glaucoma Pump-Shunt," Ophthalmic Surgery, 1990, vol. 21 (4), pp. 288-293.

Experience with Molteno-Type Shunts, Ocular Surgery News, Jun. 1, 1989, pp. 27-28.

Kakaday T., et al., "Advances in Telemetric Continuous Intraocular Pressure Assessment," British Journal of Ophthalmology, 2009, vol. 93 (8), pp. 992-996.

Krupin T., et al., "Filtering Valve Implant Surgery for Eyes with Neovascular Glaucoma," American Journal of Ophthalmology, 1980, vol. 89 (3), pp. 338-343.

Lee P., et al., "Aqueous-Venous Shunt for Glaucoma. A Further Report," Archieves of Ophthalmology, 1981, vol. 99 (11), pp. 2007-2012.

Minckler D.S., et al., "Clinical Experience with the Single-Plate Molteno Implant in Complicated Gllaucomas," Ophthalmology, 1988, vol. 95 (9), pp. 1181-1188.

Mokwa W., "Ophthalmic Implants," Sensors, Proceedings of IEEE, 2003, vol. 2, pp. 980-986.

Molteno A.C., "Use of Molteno Implants to Treat Secondary Glaucoma," 1986, pp. 211-238.

Molteno, "Seton Implant, for Management of Refractory Glaucoma," Staar Surgical Company.

Rauscher F.M., et al., "Long-term Outcomes of Amniotic membrane Transplantation for Repair of Leaking Glaucoma Filtering Blebs," American Journal of Opthammology, 2007, vol. 143 (6), pp. 1052-1054.

Wells R.G., "Tissue Mechanics and Fibrosis", Biochimica et Biophysica Acta, Jul. 2013, vol. 1832 (7), pp. 884-890.

White T.C., "A New Implantable Ocular Pressure Relief Device: A Preliminary Report," Glaucoma, 1985, vol. 7, pp. 289-294.

* cited by examiner

BLEB CONTROL GLAUCOMA SHUNTS

CROSS-REFERENCE TO RELATED PATENT APPLICATIONS

This application is a divisional of and claims priority to U.S. patent application Ser. No. 16/171,285, filed Oct. 25, 2018, which is incorporated herein by reference in its entirety.

FIELD OF INVENTION

The invention is directed to implants, and in particular to glaucoma implants comprising strip-like setons. The invention is also directed to a method for manufacturing and an insertion tool for inserting such implants.

BACKGROUND

Intraocular pressure in the eye is maintained by the formation and drainage of aqueous, a clear, colorless fluid that fills the anterior and posterior chambers of the eye. Aqueous normally flows from the anterior chamber of the eye out through an aqueous outflow channel at a rate of 2 to 3 microliters per minute.

Glaucoma is a progressive neurodegenerative disease of the eye mostly caused by a gradual increase of intraocular pressure and characterized by a gradual loss of peripheral vision. This increase in pressure is most commonly caused by stenosis or blockage of the aqueous outflow channel, resulting in excessive buildup of aqueous fluid in the eyeball. Other causes include increase in venous pressure outside the eye which is reflected back through the aqueous drainage channels and increased production of aqueous. In a "normal" eye, intraocular pressure ranges from 8 to 21 mmHg. In an eye with glaucoma, intraocular pressure can range between normal pressures up to as much as 50 mmHg. This increase in intraocular pressure produces gradual and permanent loss of vision in the afflicted eye.

Surgical procedures have been developed in an effort to treat people with glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye and eliminates the bulging of the iris that causes the angle closure. Another therapy for angle closure glaucoma is clear lens extraction and replace the crystalline lens by an intraocular lens. The extraction of the crystalline lens widens the anterior chamber angle. A trabeculotomy, opening the inner wall of Schlemm's canal, is often performed in cases of developmental or juvenile glaucoma so as to increase the outflow of the aqueous, thereby decreasing intraocular pressure. In adults, a trabeculectomy shunts fluid through a trap-door flap in the eye that performs a valve-like function for the first few weeks after surgery.

While often successful, these surgical techniques possess inherent risks associated with invasive surgery on an already afflicted eye. Furthermore, the tissue of the eye can scar over this small area and the eye reverts to the pre-operative condition, thereby necessitating the need for further treatment.

Ocular implants are often used in long-term glaucoma treatment. One early implant is described in the paper entitled "Use of Molteno Implants to Treat Secondary Glaucoma" by A. C. B. Molteno and published by Grune & Stratton, Ltd, 1986, pp 211-238. The implant was a small circular plate with a rigid translimbal drainage tube attached thereto. The plate was 8.5 mm in diameter and formed a surface area of about 100 $mm^2$. This early Molteno® implant was sutured to the sclera in the anterior segment of the eye at the limbus and the drainage tube was inserted into the anterior chamber of the eye. Once implanted, the body forms scar tissue around this plate. Fluid causes the tissues above the plate to lift and form a bleb into which aqueous flows from the anterior chamber via the drainage tube. A bleb is a fluid filled space surrounded by scar tissue.

Many problems occurred with the early Molteno® device. The bleb that formed on the sclera was elevated, which resulted in Dellen formation (sterile corneal ulcers). The implant sometimes had to be removed in another surgery to cure the ulcers. Further, this early device often did not reduce the intraocular pressure enough to treat the glaucoma without the use of additional medications.

Dr. Molteno redesigned his implant for insertion into the posterior segment of the eye to avoid the problems with his early anterior device, as disclosed in U.S. Pat. No. 4,457,757 entitled "Device for Draining Aqueous Humor." This implant is commercially available as the Molteno® Seton Implant and is also referred to as the long tube Molteno® implant. The implant comprises a flexible drainage tube connected to one or more rigid plate reservoirs, the plates are shaped to conform to the curvature of the eye. The long tube Molteno® implant is disadvantageous as the plates are formed of a rigid plastic which makes insertion beneath the eye tissue difficult and time-consuming. The reservoir plate is placed under Tenon's capsule in the posterior segment of the eye and sutured to the sclera. The drainage tube is implanted into the anterior chamber through a scleral incision.

More recently, U.S. Pat. Nos. 5,476,445 and 6,050,970 to Dr. George Baerveldt, et al. disclose glaucoma implants or shunts that include a flexible plate that attaches to the sclera and positions a drainage tube for insertion into the anterior chamber of the eye. A bleb forms around the plate and fluid drains into the bleb to regulate intraocular pressure. This type of shunt is sold as the Baerveldt® series of glaucoma implants by Johnson & Johnson Surgical Vision, Inc. of Santa Ana, Calif Other prior art glaucoma implants or shunts are known in the art. For example, the following US patents and patent publications U.S. Pat. Nos. 6,050,970; 8,353,856, 8,702,639, 8,920,357, 9,468,558, US20170020731 and US20150100010 illustrate glaucoma implants or shunt embodiments. The full disclosure of each one of these patents and patent publications is incorporated herein by reference.

The Baerveldt® device provides for pressure control with a minimally invasive surgery. The drainage tube provides a mechanism that leads excessive aqueous to the bleb formed by the seton. The seton includes fenestration holes that are designed to control bleb height and volume while a larger surface area enhances intraocular pressure (IOP) control.

Over time, the bleb may grow and cause tissue to get more fibrotic. As a result, less aqueous is passed to the body, leading to long term complication of hypertony. This becomes a positive feedback mechanism as the increase in IOP causes increased hydrostatic pressure in the bleb. The increased hydrostatic pressure results in increased tension stresses on the bleb forming tissue. The increased tension stress will lead to bleb growth and thus a further increase of the tension stresses as the inner surface of the bleb increases. The bleb growth will cause the tissue to get more fibriotic. This causes decreased diffusion of aqueous resulting in an even further increased IOP which in turn causes increased hydrostatic pressure and so forth.

The effect of hydrostatic pressure and stress on fibrotic tissue formation is also explained in the literature. For reference, see: R. G. Wells. Biochimica et Biophysica Acta 1832 (2013) 884-890. The entirety of which is herein incorporated by reference.

SUMMARY

An implantable glaucoma shunt for treating glaucoma in an eye is disclosed herein. The glaucoma shunt may comprise a plurality of strips adapted to be positioned on a sclera of the eye and an elastomeric drainage tube having an outflow end connected to the plurality of strips and an opening thereof. The drainage tube may have an open lumen and a length sufficient to extend into the anterior chamber of the eye. The plurality of strips may be substantially parallel with one another or the plurality of strips may diverge from one another. In one embodiment, the disclosed glaucoma shunt may elute an antifibrotic drug. Preferably, the shunt, including the plurality of strips, is formed of a material which is softer than 40 Shore A.

A method of manufacturing the implantable glaucoma shunt is also provided herein. The method may comprise receiving a prior-art type shunt by a material removal device. The prior-art type shunt may be spherical with an elliptical perimeter. Material may be removed from the shunt to form a plurality of strips. The strips may be removed so as to be either parallel with or divergent from each other.

The implantable glaucoma shunt may be flexible in a direction perpendicular to the surface of the eye where it will be positioned. The flexibility may cause the implantable glaucoma device to curl during implantation. The implantable glaucoma shunt may be inserted into an eye of a patient using an inserter tool to avoid deformation. The inserter tool may have an upper and lower portion for use by a surgeon to insert the glaucoma shunt. The upper and lower portion may each have a plurality of elongated grips configured to grasp each one of the strips of the shunt when pressure is applied to the upper portion and lower portion. When the inserter tool is stationary, the upper portion and lower portion may be held apart by spring tension until pressure is applied by the surgeon. The inserter may be disposable or non-disposable. In one embodiment, the inserter may act as a lancet to cut through the tissue of a patient as the shunt is being inserted. In another embodiment, the inserter may be configured with rounded tips designed to displace tissue, such as the Tenon's membrane to create space for the placement of the glaucoma shunt.

DETAILED DESCRIPTION OF THE PREFERRED EMBODIMENT(S)

Figure 1:
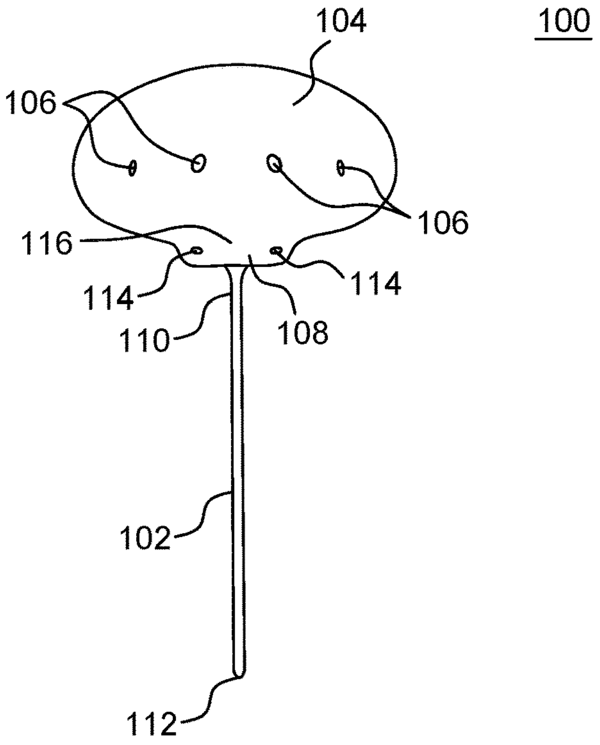
FIG. 1 (PRIOR ART)
FIG. 1 is a top-plan view of a prior art configuration of an implant.

An apparatus and method are provided to control fibrotic encapsulation of a plate of a glaucoma shunt. The apparatus reduces stress on the surrounding tissue by incorporating a modified plate shape as compared to the existing Baerveldt® glaucoma shunt device. A strip-like plate and/or thinner plate, as compared to the Baerveldt® shunt, is disclosed.

A strip-like plate to control the fibrotic reaction may reduce stress on surrounding tissue. In this way, once a bleb reaches a certain size and stress on the tissue, the mechanism is self-propelling. This mechanism may be avoided by incorporating one or more embodiments of the glaucoma shunt as disclosed herein. In contrast to the shell-like seton (section of a sphere), in one embodiment, strip-like setons are linked (either directly or indirectly) to a drainage tube.

By design, the seton of the Baerveldt® shunt is shaped as a sphere segment. In the theory of mechanics such a structure is referred to a shell. A shell is a rigid structure compared to a flat plate with the same perimeter and thickness. The rigidity of a shell-like body is explained by the higher moment of surface inertia for a deformation perpendicular to the shell surface as compared to the moment of surface inertia of a plate. A strip, for example, a beam with a length greater than width, is a less rigid structure for at least the reason that the strip has a lower moment of surface inertia in the same bending direction. That said, a series of parallel strips is also less rigid then a shell with the same surface area. Additionally, in one embodiment, thickness is reduced to reduce rigidity even further.

A strip may form a tube-like bleb which is resistant to hydrostatic pressure relative low stress. In this manner, a bleb cannot grow unlimited as the radius will be maximal half the width of the strip or sphere. The hydrostatic pressure is also not likely to blow up the bleb.

Strips may vary in width and length and preferably are curved to follow the eye sphere, inducing minimal stress. In one embodiment the length:width ratio may be 2:1 or larger. The strips can be parallel with each other or divergent from the base seton. The device can be coated with an anti-fibrotic coating or the device may elute an anti-fibrotic drug. In one embodiment, the device may be coated with 5-fluourouracil and/or mitomycin.

In one embodiment, strips may be shortened or cut off by the surgeon to match a desired IOP reduction surface need. This may be accomplished by indicating cutting lines on the device. Each one of the cutting lines may correspond to a certain area or IOP. The area may also be related with IOP by means of a nomogram or formula. In one embodiment, the cutting lines may be deeper than the surface or higher than the surface or may be textured. Thus, the cutting lines can be molded into the seton itself. Alternatively, in one or more embodiments, one or more of the plurality of strips may be removed as a whole. Each removal of a strip may alter the IOP. This can be indicated by a nomogram or formula which is included in distributed packaging and/or literature.

In one embodiment, the material used to form the shunt may be as rigid as the current Baerveldt® shunt or be made even more resilient by reducing the amount of barium sulphate. This may reduce the stress on the tissue and stress points.

An inserter is disclosed for use in implanting the strip like extensions of the seton. A strip-like seton may be more difficult to implant as is may be less stiff and the plurality of strips may be easy to bend and/or rotate. Also, each strip may require its own incision cut below the muscle to avoid scar tissue in between the strips. Hence, surgical tools may be needed to apply the incisions and to insert the device.

The design principles and embodiments disclosed herein may be combined with embodiments described in U.S. Pat. No. 8,702,639, the entirety of which is herein incorporated by reference. For example, the plate or plurality of strips may incorporate microtexturing on at least an outer or an inner face. The microtexturing may comprise an average peak-to-valley depth normal to the outer face of between about 0.5-10 microns for a periodicity in the range of 0.5 mm to 10 mm and <0.1 micron for a periodicity smaller than 0.5 mm. In another embodiment, a flow restrictor may be positioned within the drainage tube. The flow restrictor may have an open through-bore smaller than the lumen. This may immediately lower the intraocular pressure (IOP) and simultaneously prevent hypotony for at least an early post-operative period.

The plurality of strips may be created by laser cutting using, for example, a femto second laser. The cutting may be applied to an existing or current seton. In addition, a seton may be produced by molding, milling, laser cutting, waterjet cutting or additive manufacturing, for example, 3-dimensional (3D) printing.

In one alternative use, the design principle of parallel strips may also be applied in bleb control of blebs formed in the conjunctiva with laser glaucoma surgery including minimal invasive glaucoma surgery (MIGS) MIGS-implants. The embodiments disclosed herein may be applicable to any area, field or use involving the construction of any bleb and for drug release purposes.

FIG. 1 is a top-plan view of a prior art configuration of an implant 100. FIG. 1 shows an implant 100 having a plate 104 which is generally spherical in shape with an elliptical perimeter. The surface area of the plate 104 is approximately 100 to 600 $mm^2$ depending on glaucoma conditions and the radius of curvature of the plate 104 may be 12 to 14 mm. The surface area of the plate 104 may be between 250 $mm^2$ and 450 $mm^2$. It should be noted that the current Baerveldt® implant, model no. BG-101-350 has a surface area of 350 $mm^2$. When the plate 104 is pressed flat, the plate may have a length of between 20-40 mm and a width of 15-20 mm. The underside of the plate 104 may be curved in such a way to conform to the curvature of a human eye. Plate 104 includes an extension 108 for coupling a drainage tube 102. The plate 104 may include fenestrations 106, or small holes, on the surface of the plate. The fenestrations 106 are shown centered about the implant plate 104 but may be located in other areas as well. The plate 104 is attached to a first end 110 of the drainage tube 102. Drainage tube 102 also includes a second end 112. The extension 108 of plate 104 also includes two small suture holes 114 and a raised ridge 116 formed adjacent one of the larger-radius perimeter edges of the plate 104. The thickness of the plate 104 may be in the range of 0.5 to 2.0 mm.

Figure 2:
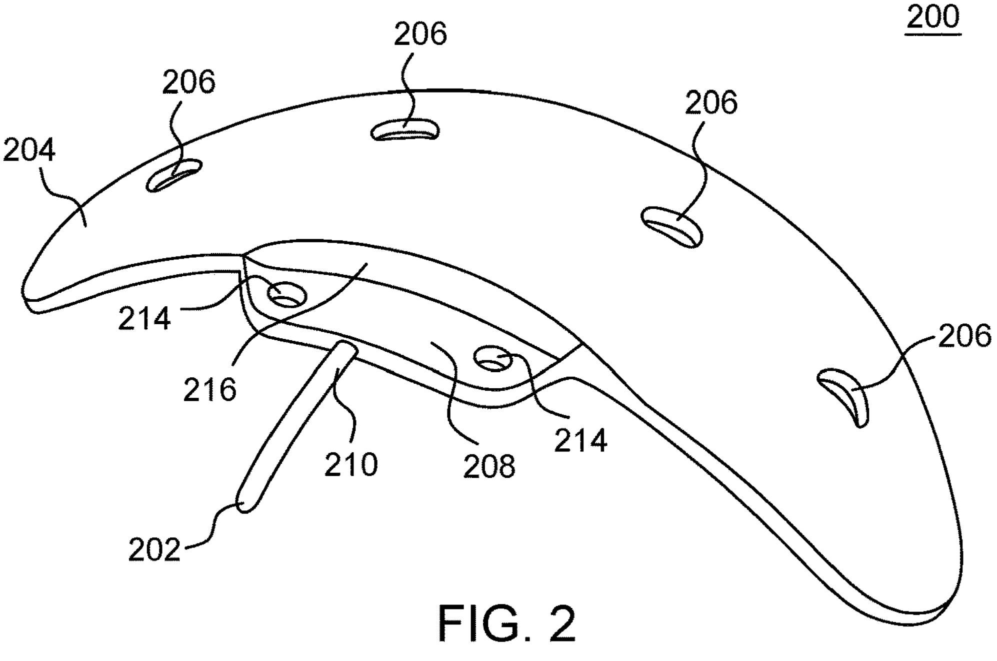
FIG. 2 (PRIOR ART)
FIG. 2 is a perspective view illustrating the plate of FIG. 1 in three dimensions.
Figure 8:
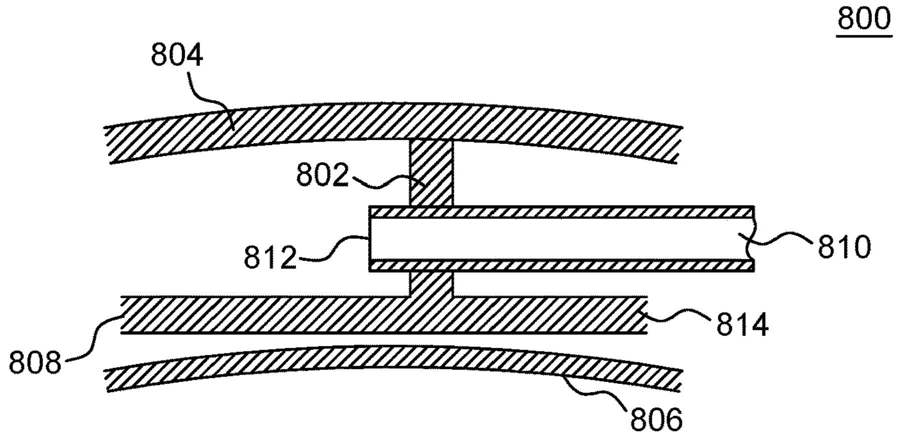
FIG. 8 is a side-plan side view of device showing the inlet of tube and the side of one strip.

FIG. 2 is a perspective view illustrating a prior art plate 200 in three dimensions. FIG. 2 illustrates a raised ridge 216 formed adjacent extension 208. Raised ridge 216 is also illustrated in FIG. 8. As shown in FIG. 2, raised ridge 216 is formed adjacent one of the larger-radius perimeter edges of the plate 204, on the curved spherical surface of the plate 204. The rounded edge of the plate 204 extending on either side of the raised ridge 216, not including that portion of the plate 204 adjacent the raised ridge 216, may be entirely radiused, tapered and blended. An extension 208 of the plate 204 is formed adjacent the raised ridge 216 in the plate 204 and includes two small suture holes 214. Drainage tube 202 comprises first end 210 extending from extension 208. Four fenestration holes 206 may be cut or drilled on the top of plate 204.

Figure 3:
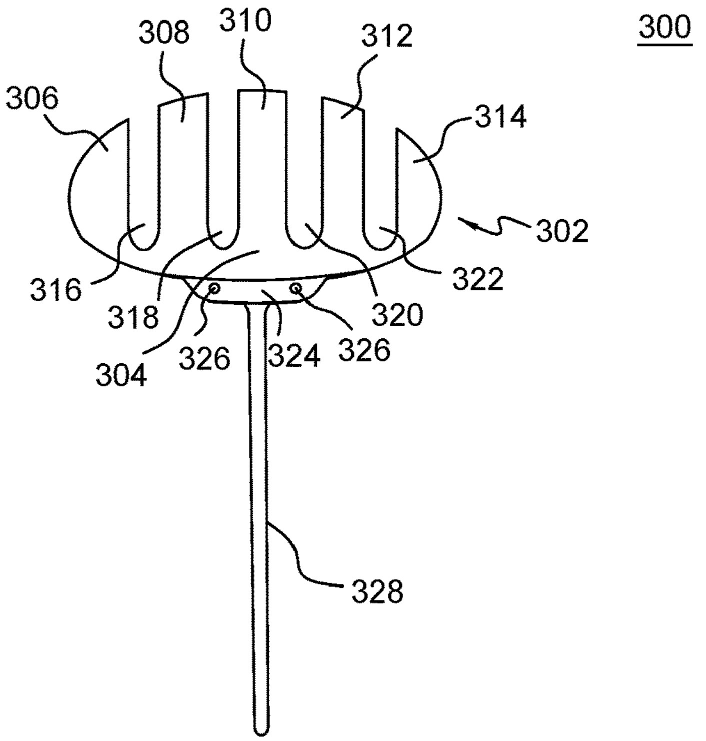
FIG. 3 is a top-plan view of a parallel strip configuration of an implant.

FIG. 3 is a top-plan view of a parallel strip configuration of an implant 300. As shown in FIG. 3, the implant 300 maintains a curvature 302 of prior art devices yet comprises a series of parallel strips 306-314. These parallel strips 306-314 make the implant less rigid as compared to the prior art, i.e. plate 104 and plate 204 of FIGS. 1-2. A thickness reduction may also help reduce overall rigidity of the plate 304. Parallel strips 306-314 may be formed via removal of material from a prior art plate 114, 204. In the example shown in FIG. 3, four sections of material 316-322 may be removed from plate 304 to form the series of parallel strips 306-314. Remaining elements of implant 300 may be similar or identical to FIGS. 1-2. For example, plate 304 may comprise an extension 324 with suture holes 326. The extension 324 may be coupled to a drainage tube 328. In an embodiment, the implant of the present invention may be molded to create the series of parallel strips.

Figure 4:
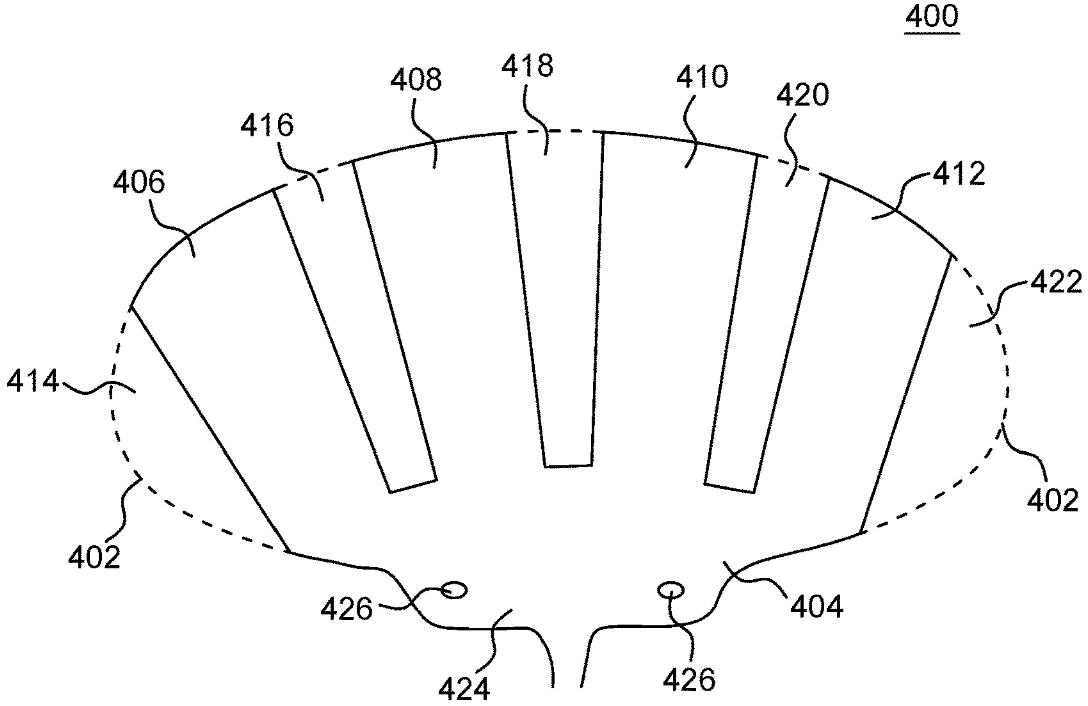
FIG. 4 is a top-plan view of a perpendicular strip configuration of an implant.

FIG. 4 is a top-plan view of a perpendicular strip configuration of an implant 400. As shown in FIG. 4, the implant 400 comprises a series of strips which would intersect if extended along an imaginary axis. FIG. 4 includes a dotted line 402 to illustrate outer diameter of plate 114 of FIG. 1 and plate 204 of FIG. 2. Alternating strips 406-412 make the implant less rigid as compared to one with a plate of FIGS. 1-2. Strips 406-412 may be formed via removal of material from a prior art plate 104, 204. In the example shown in FIG. 4, five sections of material 414, 416, 418, 420, and 422 may be removed to form the series of strips 406, 408, 410, and 412. In any embodiment described herein, one or more of strips 406, 408, 410, and 412 may be parallel to each other, substantially parallel, and/or divergent from each other. Remaining elements of implant 400 may be similar or identical to FIGS. 1-2. For example, plate 404 may comprise an extension 424 with suture holes 426 much like the prior art.

Figure 5A:
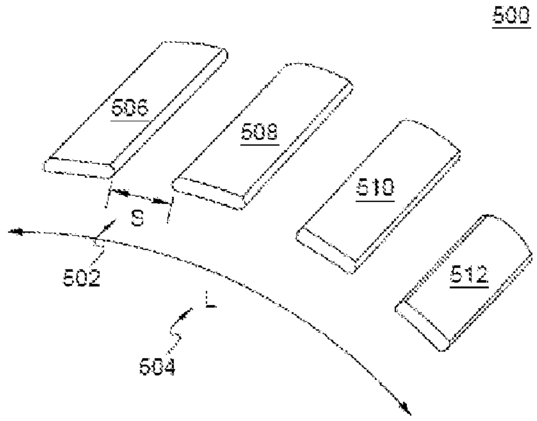
FIG. 5A is a side view of a parallel strip configuration of an implant.

FIG. 5A is a side view of a parallel strip configuration of an implant 500. In the embodiment, shown in FIG. 5A, space (S) 502 represents an individual space width between two adjacent strip segments 506, 508 and length (L) 504 represents a total length of the implant 500. Strips 506-512 are shown to be in accordance with the curvature of the human eye, although the FIG. 5A is not to scale.

Figure 5B:
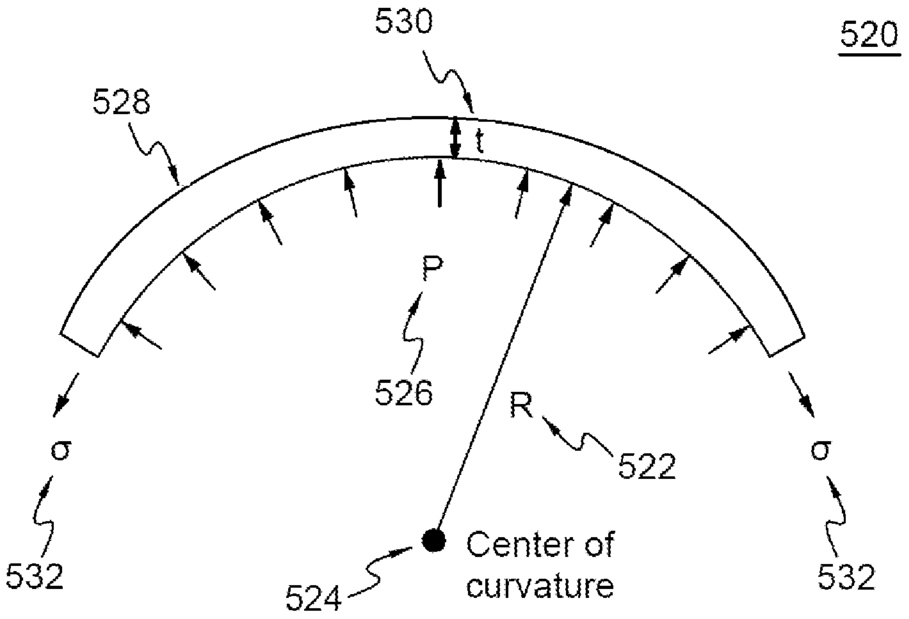
FIG. 5B is an illustration which shows that as pressure is reduced, bleb growth is also reduced.

FIG. 5B is a drawing 520 which illustrates that as the hydrostatic pressure increases, bleb 528 also increases in size. The main dimensional property is the radius of curvature 522 of the bleb 528 extending from the center of curvature 524. Bleb 528 of FIG. 5B is simplified as a hemisphere for illustrating the mechanical principles. As shown in FIG. 5B, pressure 526 builds on the bleb 528 having a thickness (t) 530. Tensile stress (σ) 532 increases accordingly.

The following equations mathematically illustrate the goal of maintaining diffusion while lowering the covered tissue surface and minimizing a size of the implant. Further, avoidance of stress on tissue of a patient is achieved by minimizing bleb growth. In addition, by making the implant smaller, it may be easier for a surgeon to implant.

In Equation 1, tensile stress (σ) is equal to (pressure (P)×radius (R))/(2×thickness (t)). This follows from the equilibrium equation of stress and hydrostatic pressure in spherical vessels as illustrated by Young, Warren C. (1989). *Roark's Formulas of Stress and Strain*. McGraw-Hill Education. Chapter 12.2, Table 28.3. The entirety of which is herein incorporated by reference.

$$\sigma = \frac{P \cdot R}{2 \cdot t} \quad \text{Equation 1}$$

Equation 1, illustrates that the bleb follows the mechanics of a hydrostatic pressure against a spherical surface. When the pressure P increases the tensile stress a will increase. The bleb is not behaving entirely as a rigid vessel, but rather as an elastic body comparable to a balloon. The tensile stress will result in elastic strain and the tissue will be stretched and the bleb size, represented by radius R, will increase until a new equilibrium is achieved.

$$\Delta R = \frac{P \cdot R^2 \cdot (1 - v)}{2 \cdot E \cdot t} \quad \text{Equation 2}$$

Where ΔR is the change in radius, P is the hydrostatic pressure, v is Poisson's ratio of the tissue material, E is the E-modulus of the tissue material and t is the thickness of the tissue. The strain will induce a fibrotic reaction of the tissue for example by exceeding an elastic strain limit of the tissue or the mechanism laid out in R. G. Wells. Biochimica et Biophysica Acta 1832 (2013) 884-890, to reduce the tensile stress. This leads to the decrease of the diffusion and the increase of the hydrostatic pressure P. When the bleb dimensions, represented by the radius R is smaller, equation 1 shows that also the tensile stress is lower, and Equation 2 shows the strain is lower and the critical strain of the tissue is less likely to be reached. A smaller initial bleb size or radius can be achieved by multiple smaller blebs (smaller radii) with the same diffusion area as the original bleb or by having instead of a spherical bleb a plurality of tube shaped blebs again with a small radius of the cross section.

To control the height of the bleb, the Baerveldt® shunt has fenestration holes. After implantation, tissue will grow through these holes and connect the inner surfaces of the roof and floor side of the bleb. With the strip design implant the function of the fenestration holes is fulfilled with the gap area between the strips. The total force that is axially exerted on the tissue filling the gaps between the strips is proportional with the pressure P and the area of the strips. If the length of the device is L, the number of strips is n, the width of the strips is w and the length of the strips is 1, the force on the gap tissue is the following $$F = P \cdot n \cdot w \cdot l \quad \text{Equation 3}$$

Equation 3 shows that the force exerted on the gap tissue will increase with the total area of the strips as defined by the number of strips or the dimension of the strips.

The axial stress $\sigma_{axial}$ is the force F exerted on the gap tissue divided by the cross section of that area. The area of the gaps is defined by the number of gaps n', the length l' and width w' of the gaps.

$$\sigma_{axial} = \frac{F}{n' \cdot w' \cdot l'} \quad \text{Equation 4}$$

$$n' = n - 1 \quad \text{Equation 5}$$

Equation 4 shows that the axial stress on the gap tissue can be reduced by increasing the total gap area. That the number of gaps is the same as the number of strips n minus 1 (as shown in Equation 5) and the length of the gaps l' is the same as the length of the strips l. The total gap area can be changed by the gap width w'. If the perimeter of the device changes from rectangular to another shape e.g. ovoid, the increase of w'/w will reduce the axial stress on the gap tissue provided the hydrostatic pressure does not change. The length of gap will be comparable with the average length of the neighboring strips.

Figure 6A:
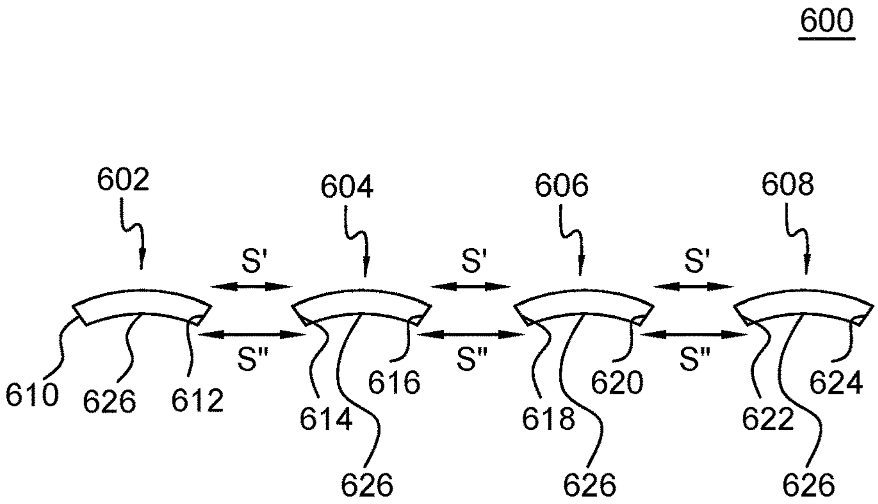
FIG. 6A side-plan view of a parallel strip configuration of an implant.

FIG. 6A side-plan view of a parallel strip configuration of an implant 600, the side-plan view being of the implant strip tips 600 shown in a tapered configuration. In this embodiment, strips are tapered such that spacing along an eye tissue, S", is greater than upper most spacing, S', of implant strips. This is accomplished by tapering strip sides 610-624 inward toward the eye. For example, strip 602 is tapered 610, 612 such that less material is present on the eye facing surface 626. The same is true for strips 604-608 shown at taper 614-624. This embodiment may be beneficial as less material is in contact with the eye tissue as compared to an embodiment in which strips are not tapered.

Figure 6B:
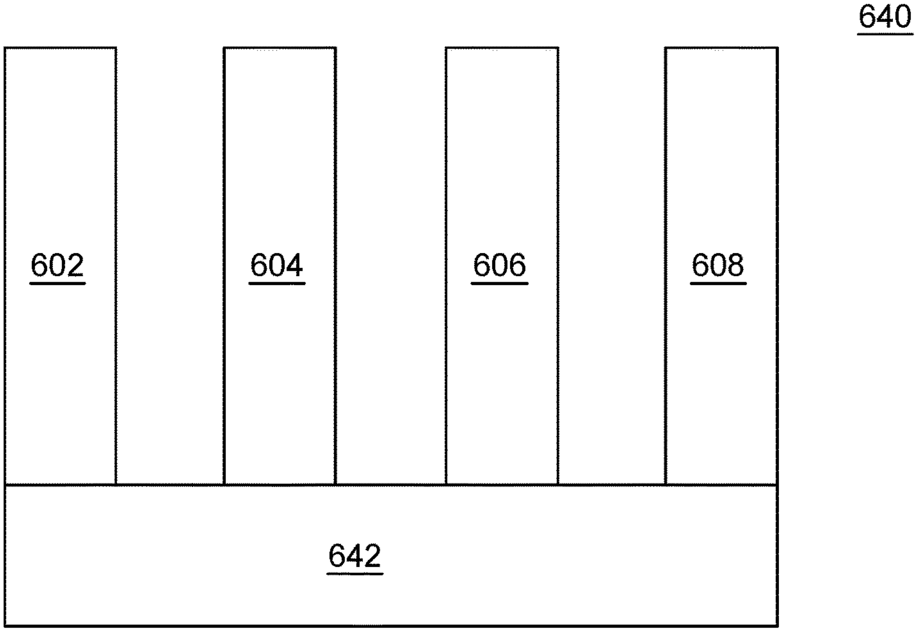
FIG. 6B is a top-plan view corresponding to FIG. 6A.

FIG. 6B is a top-plan view 640 corresponding to the implant 600 FIG. 6A. From the top-plan view, tapered portions 610-624 of FIG. 6A are unseen. In the embodiment shown in FIG. 6B, seton base section 642 occupies less surface area than in other embodiments. In some embodiments, seton base section 642 may occupy roughly the same surface area as compared to any single one of strips 602-608. Alternatively, seton base section 642 may occupy more or less surface area as compared to any single strip.

Figure 7:
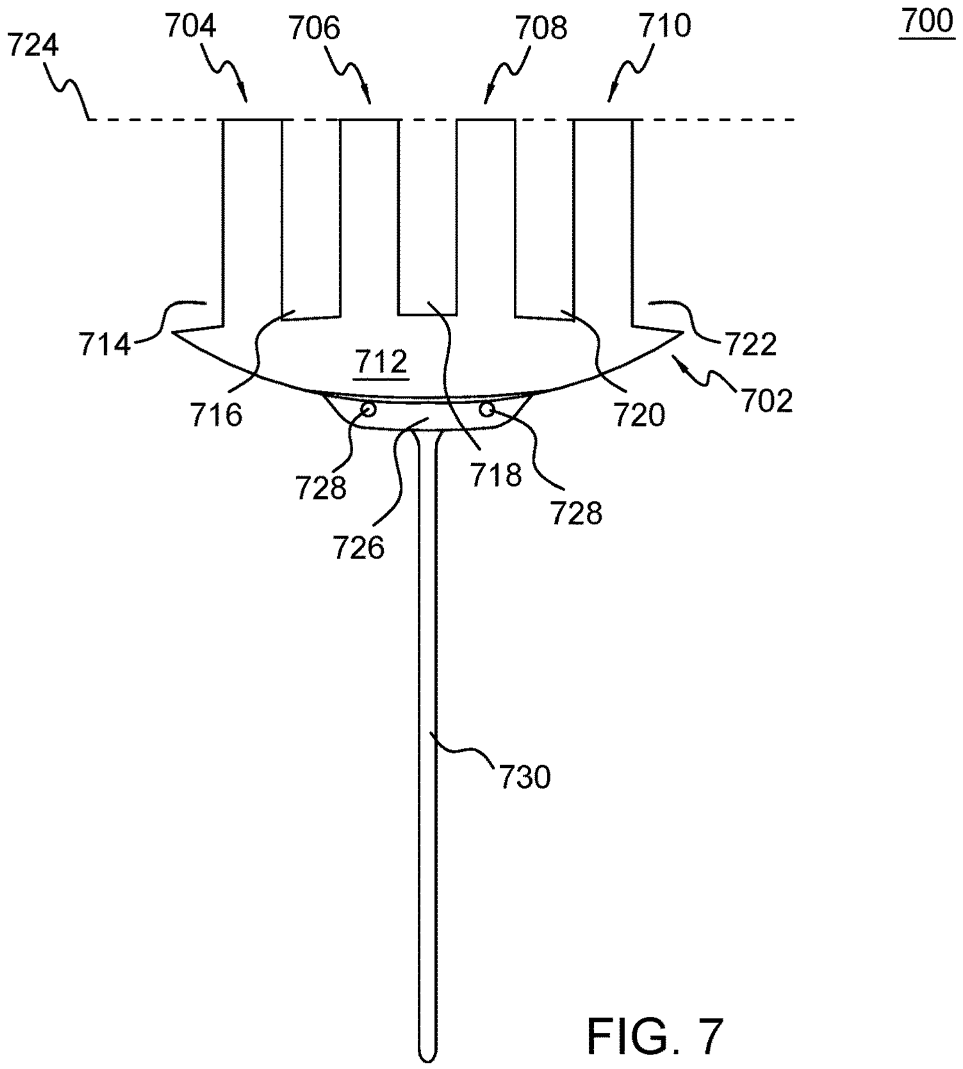
FIG. 7 is a top-plan view of an alternative parallel strip configuration of an implant.

FIG. 7 is a top-plan view of an alternative parallel strip configuration of an implant 700. As shown in FIG. 7, the implant 700 maintains only a partial curvature or ellipsis 702 of prior art devices. A series of parallel strips 704-710 are formed adjacent base portion 712 of the implant 700. These parallel strips 704-710 may achieve the goal of making the implant less rigid as compared to the prior art, i.e. FIGS. 1-2, and may also give the implant a smaller surface area as compared to alternatives. A thickness reduction may also help in reducing overall rigidity of the plate 702. Parallel strips 704-710 may be formed via removal of material from a prior art plate 114, 204. In the example shown in FIG. 7, five sections of material 714-722 may be removed from plate 712 to form the series of parallel strips 704-710. In one embodiment, a single horizontal cut 724 may be made in plate 712 to form a first plate size reduction. In another embodiment, plate 712 may be folded such that a number of cuts to remove material 714-722 may be minimized. Remaining elements of implant 700 may be similar or identical to FIGS. 1-2. For example, plate 712 may comprise an extension 726 with suture holes 728. The extension 726 may be coupled to a drainage tube 730.

FIG. 8 is a side view of an implant 800 showing an exemplary tube 810 have an outlet location 812 disposed adjacent raise ridge 802. As shown in FIG. 8, the bleb forming eye tissue 804, 806 surrounds the device on the top and bottom side. To avoid that the bleb forming tissue occludes the exit of the tube 810, the raised ridge 802 is created on the device, through which the tube 810 protrudes. Seton 808 is located below tube 810. Also, shown is extension 814.

Figure 9A:
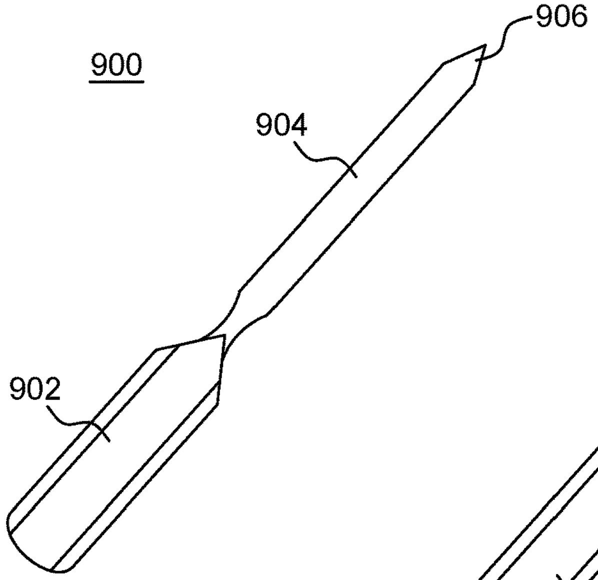
FIG. 9A is an illustration of a lancet inserter for individual or single strip insertion.

FIG. 9A illustrates a lancet inserter 900 which may be used for individual or single strip insertion. Because a strip-like seton may be more difficult to implant than the prior art devices, an inserter or lancet may be used to insert the strip like device one strip at a time. Preferably, the inserter is formed of material which has a greater stiffness than the strips and is not easy to bend and rotate.

Inserter 900 may be used for inserting a single strip at a time. Inserter 900 comprises a handle 902 and blade 904. Tip 906 of blade 904 may be designed for cutting through muscle of a patient. Preferably, lancet inserter is made of high-grade carbon steel to ensure that it can withstand repeated sterilization in high-temperature autoclaves. Alternatively, other high-quality stainless steel, chromium and vanadium alloys may be used. It may be important to ensure durability and sharpness of edges and tips for cutting through a patient's muscle tissue. In another embodiment, the inserter may be made of material suitable for disposal after a single use, e.g. plastic. In other embodiments, it may be preferable to use disposable forceps made of plastic. This may save time by allowing forceps to be disposable.

Figure 9B:
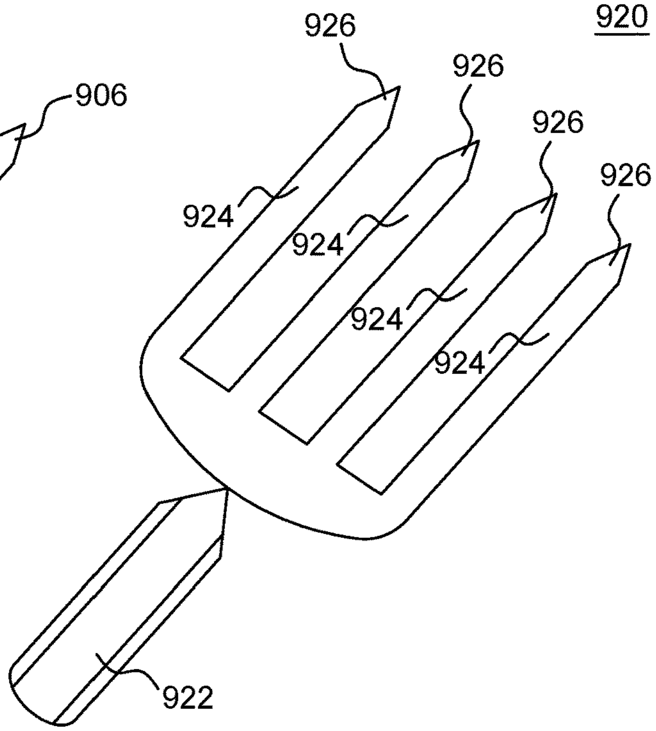
FIG. 9B is an illustration of a lancet inserter used to insert a plurality of strips simultaneously.

FIG. 9B illustrates a lancet inserter which may be used to insert all strips simultaneously. Inserter 920 comprises a handle 922, a plurality of blades 924, each having respective tips 926 for cutting muscle.

Figure 10:
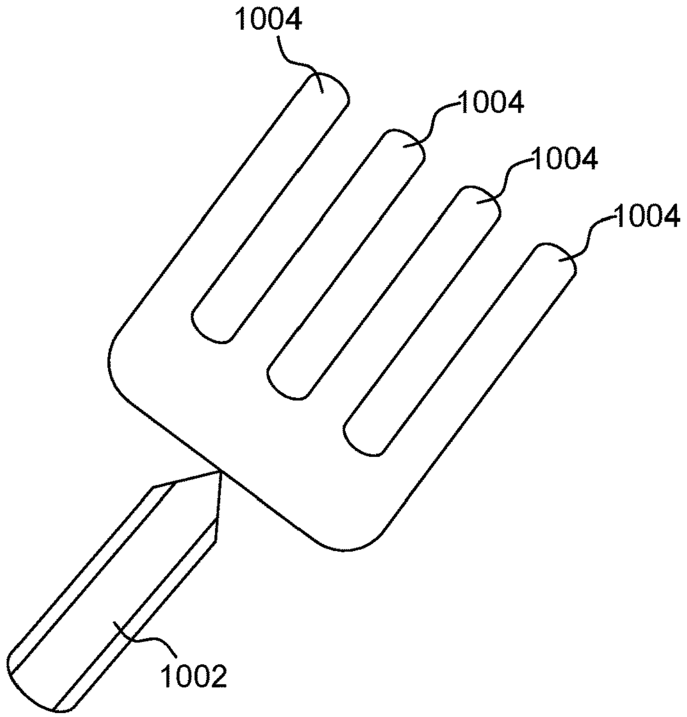
FIG. 10 is an illustration of an inserter which employs rounded tips designed to displace muscle tissue.

FIG. 10 illustrates an inserter design 1000 which employs rounded tips 1004 designed to displace, but not cut through tissue. Inserter 1000 includes a handle 1002 which may be used to insert all strips simultaneously. Tips 1004 are rounded and may be tapered in such a way to not cut through tissue.

Figure 11:
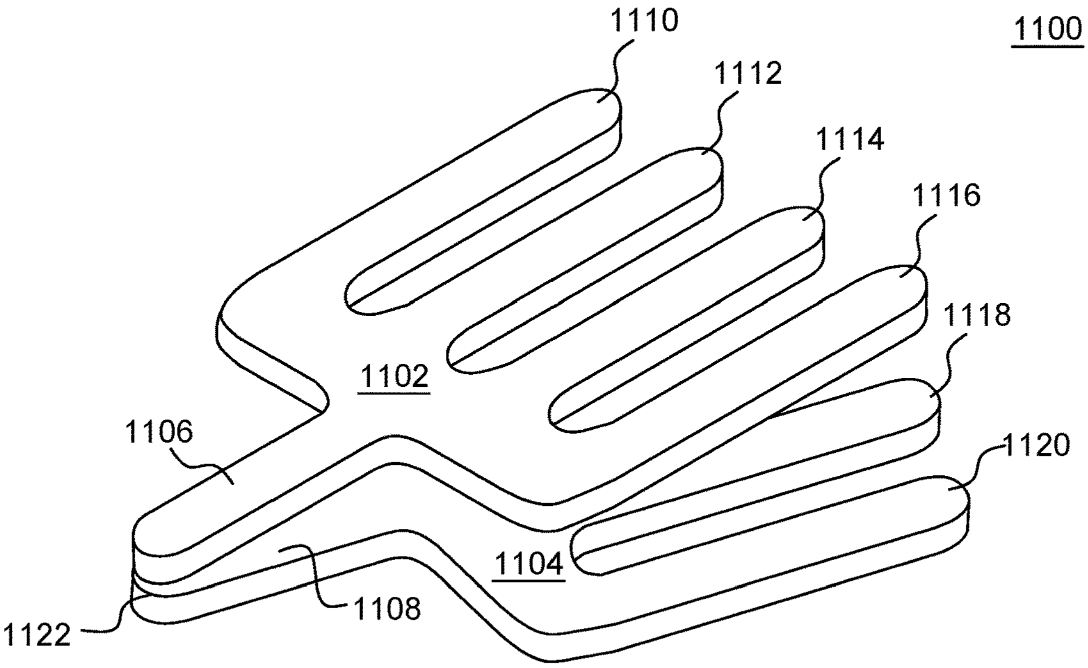
FIG. 11 is an illustration of a side view of an exemplary inserter in an open configuration.

FIG. 11 illustrates a side view of inserter 1100 in an open configuration. Inserter instrument 1100 includes an upper portion 1102 and a lower portion 1104. Handles 1106 and 1108 are configured for fingertip operation by a surgeon. Inserter may open via spring tension or any other means to accept a device for insertion. Each one of instrument tips 1110-1120 may be rounded or configured as a lancet. As shown, instrument 1100 may be elongated such that tips 1110-1120 extend beyond the shunt strips. Alternatively, instrument may be sized to match shunt strips and may even be made smaller than the shunt. Any number of tips may be used to correspond to the number of shunt strips of the device. In an embodiment, the tips and/or blades may have a shape that is similar to the shape of the shunt strips.

Inserter 1100 may be held by a surgeon between a thumb and one or two fingers of the same hand. The upper portion may rest on the tip or base the thumb, while the lower portion may rest on an adjacent tip of the index finger. Spring tension at the base end 1122 may hold the grasping ends apart until pressure is applied to upper portion 1102 and lower portion 1104. This allows a surgeon to quickly and easily grasp the shunt to insert and release it or to grasp with limited pressure. Preferably, any portion of instrument which comes in contact with the shunt will be made smooth so as to not damage the shunt. Portions which held by fingers may be etched so as to be more easily gripped by the surgeon.

Figure 12:
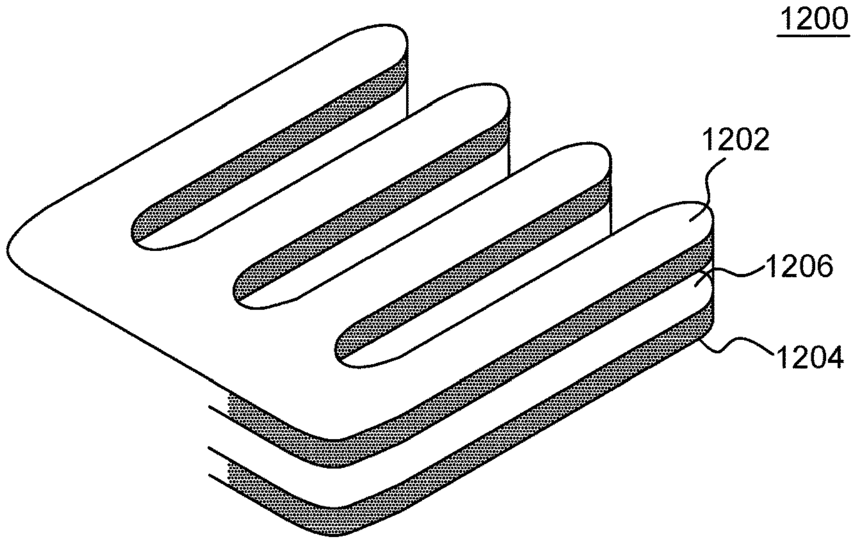
FIG. 12 is an illustration of another side view of inserter design in a closed configuration.

FIG. 12 illustrates another side view of inserter design 1200 in a closed configuration. In this configuration, instrument upper portion 1202 and lower portion 1204 grasp shunt 1206 for insertion into an eye of a patient.

While the invention has been described in its preferred embodiments, it is to be understood that the words which have been used are words of description and not of limitation. Therefore, changes may be made within the appended claims without departing from the true scope of the invention.

What is claimed is:

1. An implantable glaucoma shunt comprising:
- a plurality of strips comprising:
  - a first outer strip and a second outer strip, each comprising a curved side portion positioned away from the other of the strips; and
  - an intermediate strip positioned between the first outer strip and the second outer strip; and
- a drainage tube having an outflow end and an opening thereof, the outflow end being connected to the first outer strip, the second outer strip, and the intermediate strip;
- wherein at least two of the first outer strip, the second outer strip, and the intermediate strip are interconnected on a side proximal to the drainage tube; and
- wherein there is no interconnection between the first outer strip, the second outer strip, or the intermediate strip on a side distal to the drainage tube.

2. The implantable glaucoma shunt of claim 1, further comprising an antifibrotic drug.

3. The implantable glaucoma shunt of claim 1, wherein each strip of the plurality of strips is formed of a material which is softer than 40 Shore A.

4. The implantable glaucoma shunt of claim 1, wherein each strip of the plurality of strips has a thickness which is no greater than 0.7 mm.

5. The implantable glaucoma shunt of claim 1, configured in accordance with $n''=n-1$, wherein n represents a total number of the plurality of strips and n" represents a total number of gaps between the plurality of strips.

6. The implantable glaucoma shunt of claim 1, wherein an axial force on tissue of a gap ($\sigma_{axial}$) of the implantable glaucoma shunt is equivalent to $$\frac{F}{n'\cdot w'\cdot l'},$$

wherein F represents a force exerted on the gap tissue, n" represents a total number of gaps, w" represents a width of each gap of the gaps and l" represents a length of each gap of the gaps.

7. The implantable glaucoma shunt of claim 1, wherein the drainage tube is an elastomeric drainage tube.

8. An implantable glaucoma shunt comprising:
- a plate comprising a base portion and a plurality of strips extending from the base portion;
- wherein each one of the plurality of strips comprises a distalmost end, the distalmost end being separated from a distalmost end of an adjacent strip of the plurality of strips via a gap portion; and wherein each gap portion at the base portion is U-shaped such that a surface between at least one of the plurality of strips and another one of the plurality of strips is curved.

9. The implantable glaucoma shunt of claim 8, wherein the plurality of strips comprises a first outer strip and a second outer strip, wherein the first outer strip comprises a curved side portion and the second outer strip comprises a curved side portion.

10. The implantable glaucoma shunt of claim 8, further comprising an antifibrotic drug.

11. The implantable glaucoma shunt of claim 8, wherein each strip of the plurality of strips is formed of a material which is softer than 40 Shore A.

12. The implantable glaucoma shunt of claim 8, further comprising:

an elastomeric drainage tube having an outflow end and an opening thereof, the outflow end being coupled with the plurality of strips.

13. The implantable glaucoma shunt of claim 8, wherein each strip of the plurality of strips has a thickness which is no greater than 0.7 mm.

14. The implantable glaucoma shunt of claim 8, configured in accordance with n"=n−1, wherein n represents a total number of the plurality of strips and n" represents a total number of gaps between the plurality of strips.

15. The implantable glaucoma shunt of claim 8, wherein an axial force on tissue of a gap ($\sigma_{axial}$) of the implantable glaucoma shunt is equivalent to $$\frac{F}{n' \cdot w' \cdot l'},$$

wherein F represents a force exerted on the gap tissue, n" represents a total number of gaps, w" represents a width of each gap of the gaps and l" represents a length of each gap of the gaps.

* * * * *